United States Patent [19]

Heider et al.

[11] Patent Number: 5,587,503

[45] Date of Patent: Dec. 24, 1996

[54] PREPARATION OF SILICON-CONTAINING VINYL ETHERS AND VINYL THIOETHERS

[75] Inventors: Marc Heider, Neustadt; Jochem Henkelmann, Mannheim; Michael Karcher, Schwetzingen, all of Germany

[73] Assignee: BASF Aktiengesellschaft, Ludwigshafen, Germany

[21] Appl. No.: 518,718

[22] Filed: Aug. 24, 1995

[30] Foreign Application Priority Data

Aug. 27, 1994 [DE] Germany .................... 44 30 477.3

[51] Int. Cl.[6] .................................................. C07F 7/08
[52] U.S. Cl. ................................ 556/427; 556/445
[58] Field of Search ................................ 556/427, 445

[56] References Cited

U.S. PATENT DOCUMENTS

| | | | |
|---|---|---|---|
| 2,671,795 | 3/1954 | Frisch et al. | 556/445 X |
| 3,714,214 | 1/1973 | Hermes | 556/427 X |
| 4,033,934 | 7/1977 | Berger. | |
| 5,326,895 | 7/1994 | Kubota et al. | 556/445 |

OTHER PUBLICATIONS

Synthesis and Reaction . . . , Shotakovsky et al., Bull. Acad. Sci. USSR, (1956) 1535.
Synthesis of Dimethylorgano . . . Volkova et al., vol. 50, No. 5, Khimii, 1980.
Ulmanns Ency of Ind. Chem., 4th Ed. 1983, vol. 21, p. 498.

*Primary Examiner*—Paul F. Shaver
*Attorney, Agent, or Firm*—Keil & Weinkauf

[57] ABSTRACT

Process for preparing silicon-containing vinyl ethers and vinyl thioethers of the general formula I

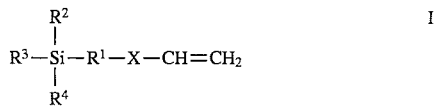

where the variables have the following meanings:

X is oxygen or sulfur, $R^1$ is $C_1$–$C_{20}$-alkylene, $C_3$–$C_{12}$-cycloalkylene or $C_6$–$C_{10}$-arylene, $R^2$, $R^3$ and $R^4$ are hydrogen, $C_1$–$C_{20}$-alkyl, $C_3$–$C_{12}$-cycloalkyl, $C_1$–$C_{12}$-alkoxy, phenoxy, heteroaryl or together with $R^1$ form a $C_3$–$C_{12}$-cycle, by reaction of silicon-containing alcohols or thiols of the general formula II

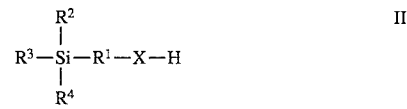

where the variables have the meaning indicated above, with acetylene, by carrying out the reaction in phenyl methyl sulfoxide, dimethyl sulfoxide, sulfolane or hexamethylphosphoramide in the presence of an alkali metal hydroxide.

4 Claims, No Drawings

PREPARATION OF SILICON-CONTAINING VINYL ETHERS AND VINYL THIOETHERS

The present invention relates to an improved process for preparing silicon-containing vinyl ethers and vinyl thioethers of the general formula I

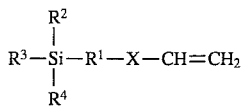

where the variables have the following meanings:

X is oxygen or sulfur, $R^1$ is $C_1$–$C_{20}$-alkylene, $C_3$–$C_{12}$-cycloalkylene or $C_6$–$C_{10}$-arylene, $R^2$, $R^3$ and $R^4$ are hydrogen, $C_1$–$C_{20}$-alkyl, $C_3$–$C_{12}$-cycloalkyl, $C_1$–$C_{12}$-alkoxy, phenoxy, heteroaryl or together with $R^1$ form a $C_3$–$C_{12}$-cycle, by reaction of silicon-containing alcohols or thiols of the general formula II

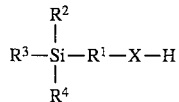

where the variables have the meaning indicated above, with acetylene.

Volkova et al. (Zh. Obshch. Khim. 50 (1980), 1067) describe the vinylation of hydroxyalkyl silicon compounds with acetylene in the presence of potassium hydroxide or of potassium. The reaction is carried out without solvents and gives only moderate yields.

Komarov et al. (Izv. Akad. Nauk. SSSR, Ser. Khim. 9 (1965), 1687) describe the vinylation of triethylsilylethylmercaptan with acetylene in dioxane in the presence of potassium hydroxide. The yield thus obtained still leaves something to be desired.

Shostakovsky et al. (Bull. Acad. Sci. USSR, Div. Chem. Sci. (1956), 1534) react 3-diethylmethylsilyl-1-propanol with acetylene in the presence of potassium methoxide in ethanol at from 170° to 180° C. to give the corresponding vinyl compound. Owing to the high temperatures, byproducts are formed which reduce the yield of the useful product sought.

U.S. Pat. No. 4,033,934 relates to the preparation of vinylthioalkylsilicones. For this, the corresponding thiols are alternatively reacted with acetylene in a solvent or without a solvent in the presence of bases such as alkali metal acetylides, alkali metals or alkali metal alkoxides or amides. Even this procedure only leads to yields which are inadequate for industrial purposes.

It is an object of the present invention to make available a process which allows the products to be prepared in high yield.

We have found that this object is achieved by an improvement of the process defined at the beginning, which comprises carrying out the reaction in phenyl methyl sulfoxide, dimethyl sulfoxide, sulfolane or hexamethylphosphoramide in the presence of an alkali metal hydroxide.

The process according to the invention can be carried out with silicon-containing alcohols and thiols of the formula II. Specifically suitable variables of the starting compounds II or of the products I are the following groups:

| | |
|---|---|
| X | sulfur or preferably oxygen; |
| $R^1$ | $C_1$—$C_{20}$-alkylene, preferably $C_1$—$C_6$-alkylene, it being possible for the alkylene radical in each case to be straight-chain or branched, such as methylene, ethylene, propylene, hexylene; $C_3$—$C_{12}$-cycloalkylene such as cyclopentylene and cyclohexylene; $C_6$—$C_{10}$-arylene such as phenylene; |

$R^2$, $R^3$ and $R^4$ independently of one another: hydrogen; $C_1$–$C_{20}$-alkyl, it being possible for the radical to be straight-chain or branched, preferably $C_1$–$C_6$-alkyl such as methyl, ethyl, n-propyl, n-butyl und n-hexyl; $C_3$–$C_{12}$-cycloalkyl such as cyclopentyl and cyclohexyl; $C_1$–$C_{12}$-alkoxy such as methoxy, ethoxy, n-propoxy; phenoxy; heteroaryl such as five- or six-membered nitrogen-containing radicals, e.g. pyridyl, pyrrolyl, quinolyl und pyrazolyl; together with $R^1$ a $C_3$–$C_{12}$-cycle, preferably a $C_5$–$C_7$-cycle.

Preferred starting compounds are those which carry $C_1$–$C_4$-alkyl or $C_1$–$C_4$-alkoxy groups on the silicon atom.

The compounds of the formula II are known or obtainable by known methods. For example, unsaturated chlorohydrocarbons can be hydrosilylated using silicon-hydrogen compounds and converted into the corresponding alcohols by hydrolysis (e.g. Collect. Czech. Chem. Commun. 37 (1972), 3885).

The compounds of the formula II are reacted with acetylene. This can be diluted with inert gases such as nitrogen, argon, carbon monoxide or propane. The molar ratio of compound II to acetylene should be at least 1:1 in order to achieve complete reaction; as a rule, however, an excess of acetylene is used.

The reaction is carried out in phenyl methyl sulfoxide, sulfolane or hexamethylphosphoramide, but preferably in dimethyl sulfoxide (DMSO). The amount of solvent is in general from 10 to 90% by weight, based on the total mixture.

The bases employed are alkali metal hydroxides such as lithium hydroxide, sodium hydroxide and preferably potassium hydroxide. As a rule, the amount is from 0.05 to 0.5 mol per mole of starting compound.

Starting compound II, solvent and the alkali metal hydroxide can be mixed and treated with acetylene. The reaction time is in general from 1 to 10 h. The temperature is as a rule from 20° to 150° C., preferably from 60° to 100° C. The acetylene pressure can be from 1 to 25 bar, preferably from 10 to 20 bar.

The reaction can be carried out continuously or batchwise in e.g. autoclaves, tubular reactors or loop reactors.

As a rule, the products I are insoluble in the solvents, so they can be isolated easily in high purity by phase separation. If appropriate, this can be followed by separation by distillation.

The solvent separated from the product can be employed again in subsequent reactions.

The products I can be employed in the same application areas as unsaturated silanes, for example as tackifiers (Ullmanns Encyklopädie der Technischen Chemie (Ullmann's Encyclopedia of Industrial Chemistry), 4th edition 1983, Vol. 21, p. 498).

The process according to the invention leads in high yield to the useful products sought. The reaction can be carried out under relatively mild conditions and permits industrially simple isolation of the products.

EXAMPLES

Example 1

Preparation of 6-(trimethylsilyl)hexyl vinyl ether

A mixture of 30 g (0.17 mol) of 6-(trimethylsilyl)hexanol, 3 g (0.05 mol) of KOH and 120 g of DMSO was heated to 80° C. in an autoclave. A pressure of 5 bar of nitrogen was applied and increased with acetylene up to a total pressure of 20 bar. Acetylene was additionally injected to the extent at which it was used. After 6 h, a two-phase mixture was obtained. The upper phase contained 6-(trimethylsilyl)hexyl vinyl ether in a purity of 97%. The conversion was 100%. After separation of the phases, the vinyl ether was obtained in a yield of 94% with a purity of 99% by distillation of the upper phase (b.p.: 104° C. (10 mbar)).

Example 2

Preparation of 3-(trimethylsilyl)propyl vinyl ether

In a similar manner to Example 1, 25 g (0.19 mol) of 3-(trimethylsilyl)propanol, 2.5 g of KOH and 25 g of DMSO were reacted at 80° C. with acetylene. 3-(Trimethylsilyl)propyl vinyl ether was obtained in 96% yield.

Example 3

Preparation of 6-(trimethylsilyl)hexyl vinyl ether

In a similar manner to Example 1, 75 g (0.43 mol) of 6-(trimethylsilyl)hexanol, 7.5 g of KOH and 75 g of DMSO were reacted at 80° C. with acetylene. 6-(Trimethylsilyl)hexyl vinyl ether was obtained in 99% yield.

Example 4

Preparation of 3-(trimethoxysilyl)propyl vinyl thioether

In a similar manner to Example 1, 30 g (0.15 mol) of 3-(trimethoxysilyl)thiopropanol, 3 g of KOH and 120 g of DMSO were reacted at 60° C. with acetylene. 3-(Trimethoxysilyl)propyl vinyl thioether was obtained in 95% yield.

Example 5

Preparation of 3-(methyldimethoxysilyl)propyl vinyl ether

In a similar manner to Example 1, 30 g (0.17 mol) of 3-(methyldimethoxysilyl)propanol, 3 g of KOH and 120 g of DMSO were reacted at 60° C. with acetylene. 3-(Methyldimethoxysilyl)propyl vinyl ether was obtained in 95% yield.

We claim:

1. A process for preparing silicon-containing vinyl ethers and vinyl thioethers of the general formula I $$\underset{R^4}{\overset{R^2}{\underset{|}{R^3-\overset{|}{Si}-R^1-X-CH=CH_2}}} \quad I$$

where the variables have the following meanings:

X is oxygen or sulfur, $R^1$ is $C_1$–$C_{20}$-alkylene, $C_3$–$C_{12}$-cycloalkylene or $C_6$–$C_{10}$-arylene, $R^2$, $R^3$ and $R^4$ are hydrogen, $C_1$–$C_{20}$-alkyl, $C_3$–$C_{12}$-cycloalkyl, $C_1$–$C_{12}$-alkoxy, phenoxy, heteroaryl or together with $R^1$ form a $C_3$–$C_{12}$-cycle, by reaction of silicon-containing alcohols or thiols of the general formula II $$\underset{R^4}{\overset{R^2}{\underset{|}{R^3-\overset{|}{Si}-R^1-X-H}}} \quad II$$

where the variables have the meaning indicated above, with acetylene, which comprises carrying out the reaction in phenyl methyl sulfoxide, dimethyl sulfoxide, sulfolane or hexamethylphosphoramide in the presence of an alkali metal hydroxide.

2. A process as claimed in claim 1, wherein the reaction is carried out in dimethyl sulfoxide in the presence of potassium hydroxide.

3. A process as claimed in claim 1, wherein the variables $R^2$ to $R^4$ are $C_1$–$C_4$-alkyl or $C_1$–$C_4$-alkoxy groups.

4. A process as claimed in claim 2, wherein the variables $R^2$ to $R^4$ are $C_1$–$C_4$-alkyl or $C_1$–$C_4$-alkoxy groups.

* * * * *